(12) United States Patent
Vollrath et al.

(10) Patent No.: US 7,268,867 B2
(45) Date of Patent: Sep. 11, 2007

(54) APPARATUS AND METHOD FOR INSPECTING A SEMICONDUCTOR COMPONENT

(75) Inventors: Wolfgang Vollrath, Burbach (DE); Thomas Krieg, Solms (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 219 days.

(21) Appl. No.: 11/076,620

(22) Filed: Mar. 10, 2005

(65) Prior Publication Data
US 2005/0219521 A1    Oct. 6, 2005

(30) Foreign Application Priority Data
Mar. 30, 2004    (DE) ............... 10 2004 015 326

(51) Int. Cl.
*G01N 21/00* (2006.01)
*G01J 3/00* (2006.01)

(52) U.S. Cl. ............... 356/237.1; 356/239.1; 356/300; 356/432

(58) Field of Classification Search ......... 356/73, 356/273.2–273.4, 300, 237, 239, 432, 448
See application file for complete search history.

(56) References Cited

U.S. PATENT DOCUMENTS

| | | | | |
|---|---|---|---|---|
| 3,645,626 A | * | 2/1972 | Druschel | 356/71 |
| 4,508,453 A | * | 4/1985 | Hara et al. | 356/394 |
| 4,518,864 A | * | 5/1985 | Inuiya | 250/208.1 |
| 4,747,608 A | * | 5/1988 | Sato et al. | 279/155 |
| 5,029,338 A | * | 7/1991 | Aichinger et al. | 378/98.7 |
| 5,371,368 A | * | 12/1994 | Alfano et al. | 250/341.1 |
| 5,403,433 A | * | 4/1995 | Morrison et al. | 216/60 |
| 5,949,927 A | * | 9/1999 | Tang | 385/12 |
| 6,057,924 A | * | 5/2000 | Ross et al. | 356/632 |
| 6,587,193 B1 | | 7/2003 | Reinhron et al. | 356/237.5 |
| 6,829,559 B2 | * | 12/2004 | Bultman et al. | 702/155 |
| 7,109,464 B2 | * | 9/2006 | Cartlidge et al. | 250/208.1 |
| 7,123,356 B1 | * | 10/2006 | Stokowski et al. | 356/237.2 |
| 2001/0021013 A1 | * | 9/2001 | Hecht et al. | 356/51 |
| 2002/0149136 A1 | * | 10/2002 | Baird et al. | 264/400 |
| 2003/0202178 A1 | | 10/2003 | Tsuji et al. | 356/237.2 |

FOREIGN PATENT DOCUMENTS

EP    0 455 857 A1    11/1991

\* cited by examiner

*Primary Examiner*—Layla G. Lauchman
*Assistant Examiner*—Jarreas Underwood
(74) *Attorney, Agent, or Firm*—Houston Eliseeva LLP

(57) ABSTRACT

Examination devices and methods operating with incident light have hitherto been used for the examination of wafers. To allow these devices also to be used with the transmitted-light method, it is proposed to configure the substrate holder (16) so that an illumination device (38, 40, 42) is integrated into the substrate holder (16) in such a way that transmitted-light illumination of the wafer (18) is possible.

18 Claims, 3 Drawing Sheets

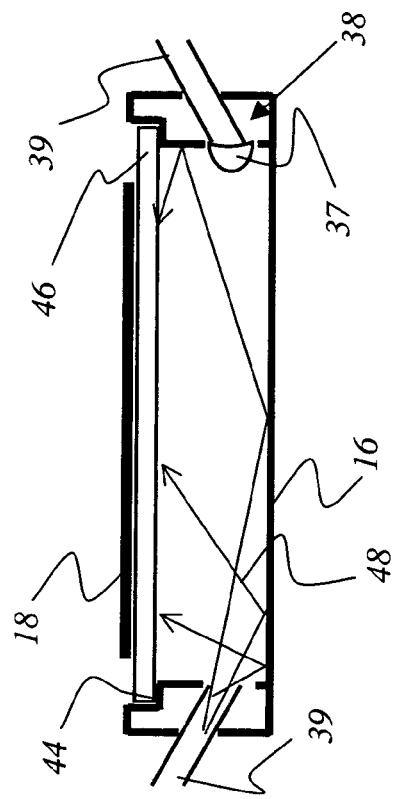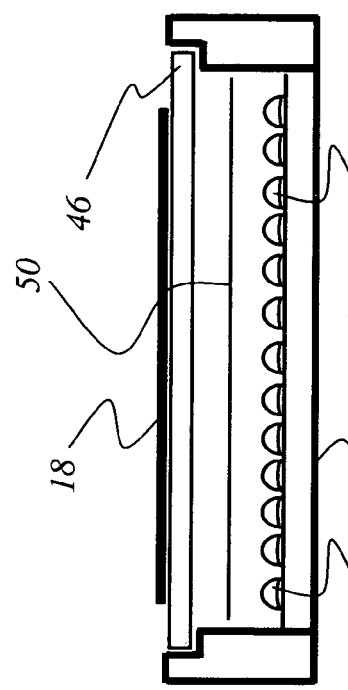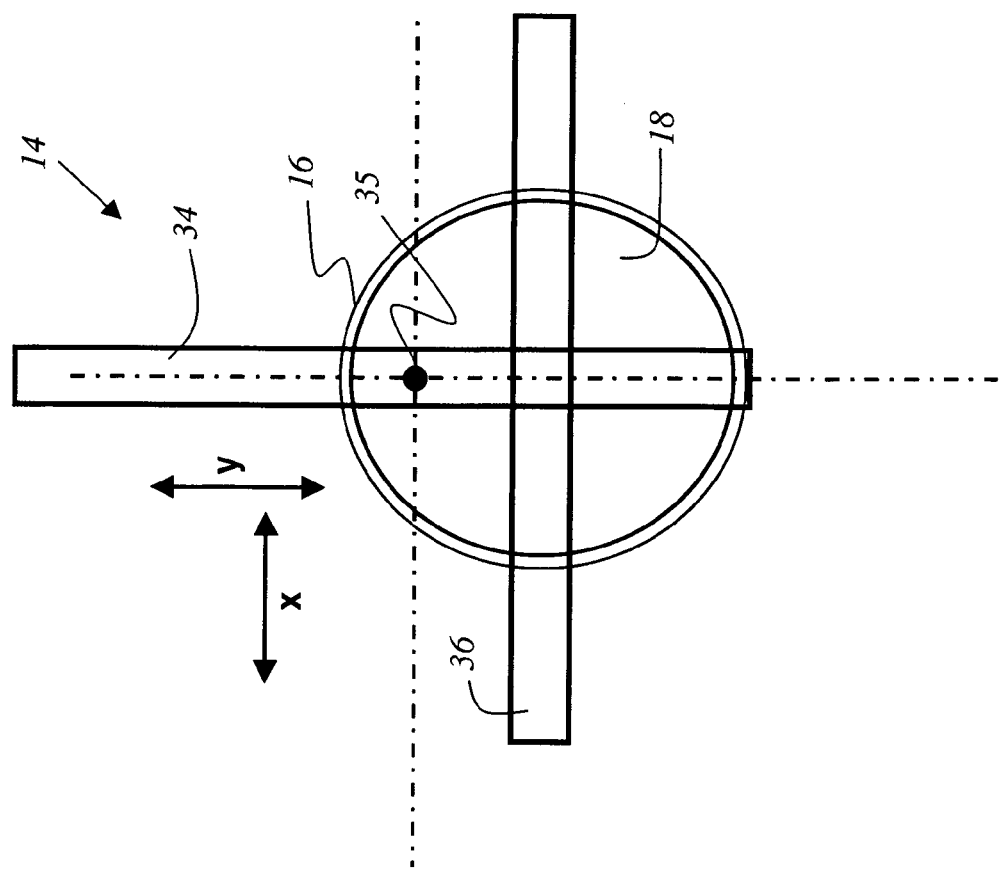

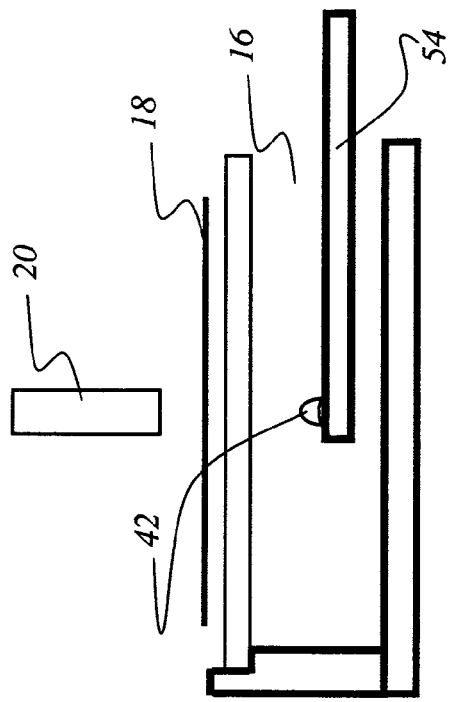
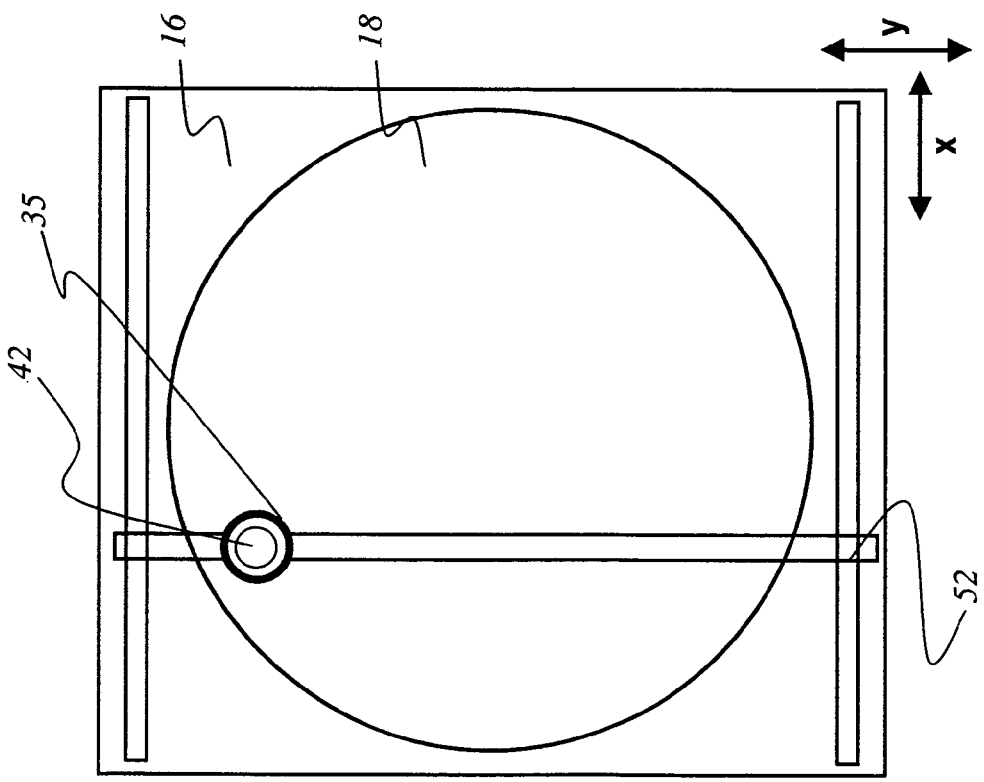

APPARATUS AND METHOD FOR INSPECTING A SEMICONDUCTOR COMPONENT

RELATED APPLICATIONS

This application claims priority of the German patent application 10 2004 015 326.4 which is incorporated by reference herein.

FIELD OF THE INVENTION

The invention concerns apparatuses for inspecting a semiconductor component, having a substrate holder on which the semiconductor component, which is a wafer or a microchip or a micromechanical component, is mounted for inspection.

The invention further concerns a method for inspecting a semiconductor component in which a substrate holder, on which the semiconductor component is mounted for inspection, is provided. The semiconductor component is observed with an observation device, in particular a microscope having at least one objective.

BACKGROUND OF THE INVENTION

Optical devices are particularly suitable for inspecting the surface of wafers. Examination of the surface can be accomplished, for example, as is known from EP 455 857, by evaluating rays that are reflected from the surface of the wafer.

Also known are optical apparatuses that, by image recognition, allow the detection of a great variety of features on the surface of a wafer or a semiconductor substrate. In this context the wafer is usually illuminated in bright-field fashion and scanned with a camera, for example a matrix camera or linear camera.

It is furthermore known from U.S. Pat. No. 6,587,193 to examine the surface of a wafer, an illumination being selected that scans the wafer in the form of a line. The illuminating line is guided over the surface of the wafer so that a two-dimensional image can be produced.

US 2003/0202178 A1 furthermore discloses a method and an apparatus for examining a wafer. Here an illumination is irradiated onto the wafer so that an edge of the wafer is struck. The edge of the wafer can thus be sensed and processed by an image processing unit. Defects of the wafer can be ascertained by a comparison of the ascertained edge image with a stored comparison image.

The known systems for inspecting a wafer are designed exclusively for incident-light inspection. The reason for this is principally that silicon wafers are opaque in the region of visible, ultraviolet, and deep ultraviolet light wavelengths. Silicon becomes transparent only at a wavelength above 1000 nm. In these wavelength regions the possibility then presents itself of being able to inspect features below the surface of the wafer, or to observe features on the front side of the wafer through the back side.

For the transmitted-light examination of wafers, however, the known illumination concepts of transmitted-light microscopy require a transmitted-light illuminating optical system below the microscope and a transmitted-light-capable microscope stage, which is not implemented in presently known examination systems. An expansion of the known examination systems to include transmitted-light inspection therefore requires a completely new design. In particular, such systems would need to be equipped with a wafer microscope stage suitable for transmitted light, which has, in contrast to the incident-light wafer microscope stages used hitherto, an unobstructed passthrough opening for the transmitted-light illumination over the entire wafer diameter. Considerable design effort for integrating a transmitted-light illumination system into the wafer inspection device is also necessary.

SUMMARY OF THE INVENTION

It is therefore the object of the present invention to develop the known wafer/semiconductor component inspection device so that it can be used for transmitted-light applications.

According to the present invention, this object is achieved by way of an apparatus for inspecting at least one semiconductor component comprising: a substrate holder that retains the semiconductor component for inspection and an illumination device for transilluminating the semiconductor component wherein the provided with the substrate holder.

It is a further object of the present invention to develop the known wafer/semiconductor component inspection method which can be used for transmitted-light applications.

The above object is accomplished by a method for inspecting a semiconductor component, comprising the steps of:

mounting the semiconductor component on a substrate holder for inspection, observing the semiconductor component, with a microscope, having at least one objective for observing the semiconductor component, illuminating the semiconductor component in a transilluminating fashion, wherein the substrate holder is equipped with an illumination device.

According to the present invention a special substrate holder is therefore provided, into which is integrated an illumination device for illuminating the wafer. The semiconductor component can encompass, for example, a wafer, a microchip, or a micromechanical component. It is self-evident that several microchips or micromechanical components are patterned onto one wafer. The term "wafer" is used for the sake of simplicity in the description that follows, but is not to be construed as a limitation. To allow the semiconductor component or wafer to be observed in transmitted light, the illumination device is embodied so that it emits light of a wavelength in the infrared wavelength region. The wafer is transparent to light in the infrared wavelength region. The substrate holder can be embodied as an attachment onto a wafer stage that is already present, if the geometrically required registrations are taken into account. The illumination device emits an illuminating light beam for illumination of the wafer. The wafer is thus illuminated from below, i.e. from the side facing away from the microscope's objective. This makes transmitted-light observation possible, while dispensing with any complex modification of the design of the overall equipment. In principle, with the apparatus and the method according to the present invention the possibility also exists of allowing observation, in transmitted light, of features in the deeper layers of the wafer and below the wafer surface. This is of great interest for quality control when packaging chips in the housing, since here the functional surface of the chip faces away from the housing surface.

In a preferred embodiment, a diffusion device is provided in order to achieve a high intensity and homogeneity in the illuminating radiation; for example, a diffusion panel; a diffusely scattering coating of, in particular, the side walls of the substrate holder; or a diffusely scattering collector optical system is used. The diffusion devices can be used singly or in combination with one another.

In an embodiment, the illumination device can encompass at least one light guide that is integrated into the substrate holder. Light of a suitable wavelength can then be guided through this light guide into the substrate holder. It is likewise possible to provide infrared light-emitting diodes, in particular in the form of a light-emitting diode matrix, in the substrate holder. The light-emitting diodes can be mounted directly on the inner side of the side wall of the substrate holder, or integrated into the latter.

For illumination of the wafer or semiconductor component, it is placed onto the substrate holder. An illuminating light beam emerges from the illumination device and then illuminates the wafer. Advantageously, the wafer is diffusely illuminated, i.e. before encountering the wafer the illuminating light beam is conveyed to a diffusion device, e.g. a glass carrier plate on which the wafer lies, a diffusion panel, a diffusely scattering coating, or a diffusely scattering collector optical system.

If the illumination device is appropriately selected, it can also be carried along in the interior of the substrate holder, so that a large-area configuration can be dispensed with. In particular, an incandescent lamp or a locally delimited light-emitting diode array, mounted on a positioning unit that is moved synchronously with the scanning stage, can be used here.

With the integrated illumination system, a wafer inspection device that permits transmitted-light illumination of the wafer is created. There is no need to redesign the scanning stage, the basic frame, or the microscope unit. On the contrary, units already on the market can in fact be retrofitted with the transmitted-light device.

BRIEF DESCRIPTION OF THE DRAWINGS

Further advantages and advantageous embodiments of the invention are the subject matter of the Figures below and their descriptions.

In the individual Figures:

FIG. 2 schematically shows a scanning stage with a wafer;

FIG. 3 schematically shows an embodiment of the substrate holder with light guides;

FIG. 4 schematically shows an embodiment of the substrate holder with light-emitting diodes;

FIG. 5 schematically shows an embodiment of the substrate holder with a movable, locally delimited illumination device;

FIG. 6 schematically shows an embodiment of the substrate holder with a locally delimited illumination device provided in stationary fashion.

DETAILED DESCRIPTION OF THE PREFERRED EMBODIMENTS

Figure 1:
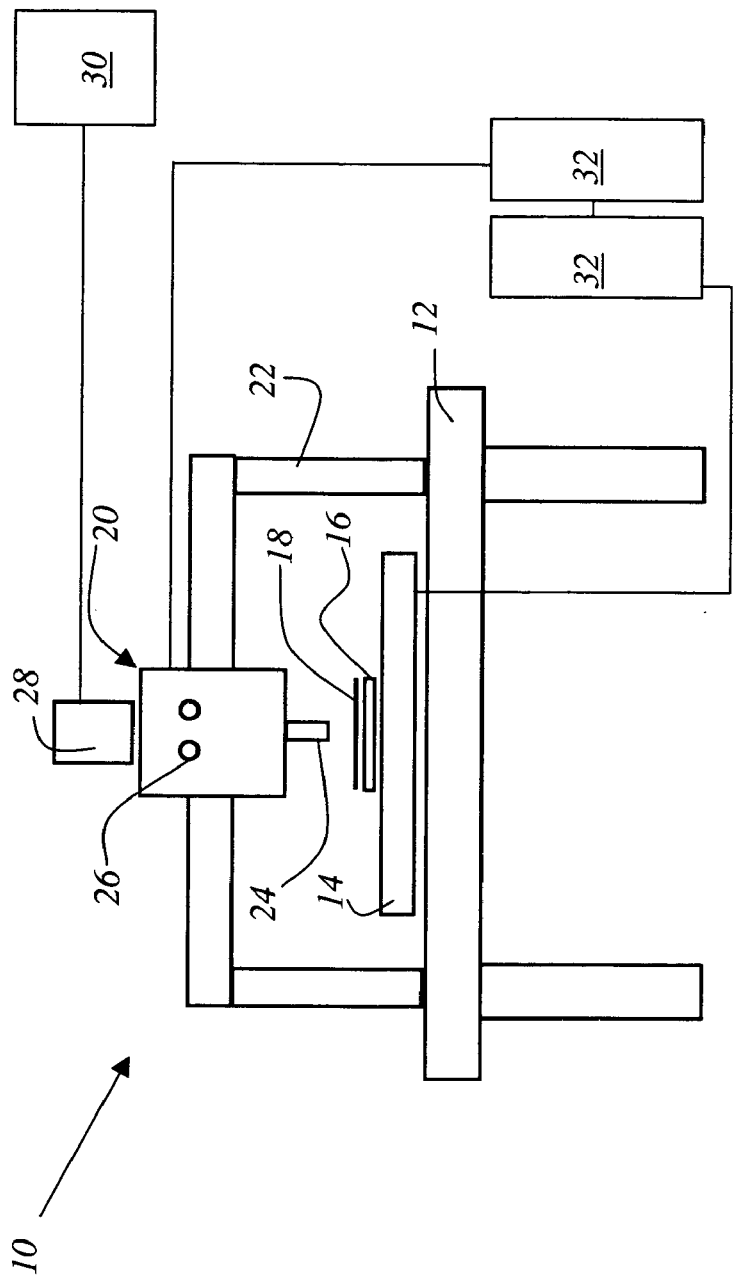
FIG. 1 is a schematic overall view of a wafer inspection device.

FIG. 1 schematically shows a characteristic configuration of a wafer inspection device 10 according to the present invention. A scanning stage 14, constituting the microscope stage, is integrated on a basic frame 12. Wafer 18 that is to be examined is placed onto or into scanning stage 14, either directly or on a substrate holder 16 located on the scanning stage. An observation device, preferably a microscope 20, is connected via a carrier unit 22 to basic frame 12 and allows magnified observation of wafer 18. Microscope 20 encompasses at least one objective 24, which represents an imaging optical system that make possible observation at different magnifications. The features observed in magnified fashion can be viewed directly via an eyepiece 26 or via a CCD camera 28 that is provided as applicable. The signals of camera 28 are transmitted for that purpose to a monitor 30. Additionally provided is an electronics unit 32 with which system automation can be achieved. Electronics unit 32 serves in particular to control scanning stage 14 or to read out camera 28.

Substrate holder 16 is usually configured so that it can receive the wafer or semiconductor component 18 under examination in such a way that is immobilized during the examination time period. According to the present invention, it comprises an illumination device that enables transmitted-light illumination of wafer 18.

As shown in FIG. 2, scanning stage 14 comprises two axes 36 and 34 that are displaceable perpendicular to one another in the X and the Y direction. Every point 35 to be observed on wafer 18 can thus be brought beneath the optical axis of microscope objective 24 (FIG. 1). Wafer 18 is immobilized on substrate holder 16, and is illuminated by the illumination device integrated into substrate holder 16.

FIG. 3 depicts substrate holder 16 in a first embodiment. Integrated into substrate holder 16 is an illumination device 38 that comprises at least one light guide 39. Substrate holder 16 is closed at the bottom, i.e. on the side facing away from wafer 18, and is open at the top, i.e. in the direction toward wafer 18. Wafer 18 can be placed, for examination, on a glass plate 46. Depending on requirements regarding the flatness of wafer 18 and the homogeneity of the illumination, however, the wafer can also be placed, without a glass plate, directly on substrate holder 16. For this, the side edges of wafer 18 are placed into support edges 44 on both sides of substrate holder 16. Small orifices through which a vacuum can be applied to wafer 18 can be provided in glass plate 46, thus making possible immobilization of wafer 18.

For illumination, light is guided through at least one light guide 39 into the interior of substrate holder 16. The side walls along the periphery of substrate holder 16 are preferably selected as the entry points. Light guides 39 are oriented with an inclination from top to bottom but can also enter substrate holder 16 from bottom to top, or horizontally. An illuminating radiation 48 whose wavelength lies in the infrared emerges from light guide 39. Illuminating radiation 48 is diffusely reflected at the inner walls of substrate holder 16 and thus travels from bottom to top, through glass plate 46 if applicable, through wafer 18. To maximize the intensity and homogeneity, the inner walls of substrate holder 16 can be provided with a highly reflective diffusely reflecting layer, which then constitutes a diffusion device. At the exit surface of light guide 39, a collector optical system 37 can be provided as a part of illumination device 38. With that system, the emission characteristics can be optimally adapted to the geometric interior configuration of substrate holder 16. In addition, collector optical system 37 itself can already have diffusely scattering properties that can be brought about, in particular, by way of a roughened surface. For better homogenization of illuminating radiation 48, glass plate 46 can also have such diffusely scattering properties.

A further embodiment of the wafer stage is depicted schematically in FIG. 4. Light-emitting diodes 40 are provided here as the illumination device. The illuminating light is preferably produced entirely in the interior of substrate holder 16, light-emitting diodes 40 arranged in planar fashion being provided on the floor of substrate holder 16. An embodiment in which light-emitting diodes 40 are provided in the form of a planar light-emitting diode matrix is particularly suitable here. To improve illumination homogeneity in the plane of wafer 18, a diffusion panel 50 can be arranged between light-emitting diodes 40 and wafer 18. Alternatively or additionally, glass plate 46 can once again have diffusing properties.

Because undesirable heat occurs as a result of the operation of light-emitting diodes 40, a further advantage can be achieved with the aid of a control device, for example electronics unit 32. For this purpose, the control device controls light-emitting diodes 40 in such a way that only those particular diodes currently located beneath observation point 35 (FIG. 2) emit light. The result is that heat evolution is greatly reduced even though illumination is adequate and homogeneous. Only a subset of the light-emitting diodes that are present is therefore used to illuminate wafer 18.

The actions already cited for the homogenization of illuminating radiation 48 are to be regarded as examples. In general, all methods known for producing a homogeneous background illumination can be used, especially those that are applied in LCD flat-screen monitors. Glass plate 46 need not necessarily be made of glass. On the contrary, any material can be used that is transparent to the illuminating rays 48 utilized in each case.

A further embodiment of substrate holder 16 is depicted schematically in FIG. 5. The illumination device used in this embodiment is a locally delimited light source, for example a conventional incandescent lamp 42 or a locally delimited light-emitting diode array. Incandescent lamp 42 is positioned beneath the respective point 35 to be observed so that the latter is sufficiently illuminated. For that purpose, the incandescent lamp is brought to observation point 35, preferably synchronously with the scanning stage, via an X-Y positioning unit 52 inside substrate holder 16. In particularly preferred fashion, a unit that comprises the actual light source as well as a collector optical system having optionally diffusing properties in order to homogenize the illumination can be used as the illumination source. The illumination device can thus, concretely, comprise a locally delimited light-emitting diode array together with a collector optical system.

In a further preferred embodiment of substrate holder 16, the locally delimited illumination source 42 can also be arranged in stationary fashion relative to microscope 20. This is depicted in FIG. 6. Substrate holder 16 is embodied here not as a completely closed cylinder, but as a component that is U-shaped in cross section. As in all the embodiments hitherto described, substrate holder 16 can move together with scanning stage 14 (FIG. 1) during positioning. Light source 42 is held on carrier arm 54 which is located between the limbs, i.e. the upper and the lower side, of the U-shaped substrate holder 16. This ensures that carrier arm 54, and therefore light source 42, can be positioned as desired without resulting in collisions. An advantage of this embodiment is that an X-Y positioning unit can be eliminated, as can a large-area light-emitting diode array that generates a great deal of heat and entails high energy consumption.

Alternatively, illumination device 38 can be embodied as a light-guiding cable guided along carrier arm 54 and having a deflection and homogenization optical system mounted at the exit end, and an incoupling of light outside substrate holder 16 can be utilized.

What is claimed is:

1. An apparatus for inspecting at least one semiconductor component comprising:
   a substrate holder for retaining the semiconductor component for inspection; and
   an illumination device for transilluminating the semiconductor component, wherein the illumination device is integrated into the substrate holder.

2. The apparatus as defined in claim 1, wherein the semiconductor component comprises a water, a microchip, or a micromechanical component.

3. The apparatus as defined in claim 2, wherein several microchips or micromechanical components are patterned onto one wafer.

4. The apparatus as defined in claim 1, wherein a diffusion device is provided in order to achieve diffuse irradiation of the semiconductor component.

5. The apparatus as defined in claim 4, wherein a glass carrier plate, a diffusion panel, a diffusely scattering coating, and/or a diffusely scattering collector optical system is provided as the diffusion device.

6. The apparatus as defined in claim 4, wherein the wafer on which the semiconductor component is disposed functions as the diffusion device.

7. The apparatus as defined in claim 1, wherein the substrate holder is equipped with a glass carrier plate.

8. The apparatus as defined in claim 1, wherein the illumination device comprises a light-guiding cable and optionally a collector optical system.

9. The apparatus as defined in claim 8, wherein at least two light-guiding cables are guided into the substrate holder from bottom to top in inclined fashion from top to bottom or horizontally.

10. The apparatus as defined in claim 1, wherein the illumination device is embodied as a light guide guided along a carrier arm and having a deflection and homogenization optical system mounted at an exit end of the carrier arm.

11. The apparatus as defined in claim 1, wherein light-emitting diodes in the form of an infrared light-emitting diode matrix are provided as the illumination device.

12. The apparatus as defined in claim 11, wherein the light-emitting diodes are inserted along the periphery of the substrate holder directly into a substrate holder's inner side wall.

13. A method for inspecting a semiconductor component, comprising the steps of:
   mounting the semiconductor component on a substrate holder for inspection;
   observing the semiconductor component with a microscope having at least one objective for observing the semiconductor component; and
   illuminating the semiconductor component with an illumination device in a transilluminating fashion, wherein the illumination device is integrated into the substrate holder.

14. The method as defined in claim 13, wherein the semiconductor component comprises a wafer, a microchip, or a micromechanical component.

15. The method as defined in claim 14, wherein several microchips or micromechanical components are patterned on one wafer.

16. The method as defined in claim 13, further comprising homogenizing the illuminating light beam with a diffusion device in the form of a glass carrier plate, a diffusion panel having a diffusely scattering coating, and/or a diffusely scattering collector optical system prior to illuminating the semiconductor component.

17. The method as defined in claim 13, wherein the wafer on which the semiconductor component is disposed functions as a diffusion device.

18. The method as defined in claim 13, wherein an incandescent lamp or a locally delimited light-emitting diode array is used as the illumination device, and the illumination device is brought to the observation point, synchronously with the scanning stage, via a displaceable positioning unit inside the substrate holder.

* * * * *